(12) United States Patent
Karras

(10) Patent No.: US 6,727,064 B2
(45) Date of Patent: *Apr. 27, 2004

(54) ANTISENSE OLIGONUCLEOTIDE MODULATION OF STAT3 EXPRESSION

(75) Inventor: James G. Karras, San Marcos, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 09/758,881

(22) Filed: Jan. 11, 2001

(65) Prior Publication Data

US 2001/0029250 A1 Oct. 11, 2001

Related U.S. Application Data

(63) Continuation-in-part of application No. PCT/US00/09054, filed on Apr. 6, 2000, which is a continuation of application No. 09/288,461, filed on Apr. 8, 1999, now Pat. No. 6,159,694.

(51) Int. Cl.[7] .................................................. C12Q 1/68
(52) U.S. Cl. .......................... 435/6; 435/325; 435/375; 536/23.1; 536/24.5
(58) Field of Search ................. 514/44, 23.1; 536/24.3, 536/24.32, 24.5; 435/6, 325, 375

(56) References Cited

U.S. PATENT DOCUMENTS 5,719,042 A  2/1998  Kishimoto et al. ........ 435/69.1
5,801,154 A * 9/1998  Baracchini et al. ........ 435/325
5,844,082 A  12/1998  Kishimoto et al. ......... 530/350
6,159,694 A * 12/2000  Karras ........................ 435/325

OTHER PUBLICATIONS

Grandis, J.R. et al., J. Clin. Inv. 102(7) 1385–1392.*
Agrawal, S. Trends Biotechnol. Oct. 1996; 14(10):376–87.*
Gewirtz et al., Proc. Natl. Acad. Sci. v 93, pp. 3161–3163.*
Braasch, D. A. Biochemistry. Apr. 2002; 41(14): 4503–4510.*
Branch, A.D., (1998). Trends Biochem Sci. Feb. 1998;23(2):45–50.*
Tamm, I. et al. The Lancet. Aug. 2001, 358: 489–497.*
Grandis et al., "Requirement of Stat3 but not Stat1 Activation for Epidermal Growth Factor Receptor–mediated cell growth in Vitro", *J. Clin. Invest.* 1998 102:1385–1392.
Lamy et al., "Dysregulation of CD95/CD95 Ligand–Apoptotic Pathway in CD3+ Large Granular Lymphocyte Leukemia", *Blood* 1998 92 (12) :4771–4777.

* cited by examiner

Primary Examiner—Sean McGarry
Assistant Examiner—James Douglas Schultz
(74) Attorney, Agent, or Firm—Licata & Tyrrell P.C.

(57) ABSTRACT

Compounds, compositions and methods are provided for inhibiting the expression of human STAT3. The compositions comprise antisense oligonucleotides targeted to nucleic acids encoding STAT3. Methods of using these oligonucleotides for inhibition of STAT3 expression and for promotion of apoptosis are provided. Methods for treatment of diseases, particularly inflammatory diseases and cancers, associated with overexpression or constitutive activation of STAT3 or insufficient apoptosis are also provided.

15 Claims, No Drawings

ANTISENSE OLIGONUCLEOTIDE MODULATION OF STAT3 EXPRESSION

This application is a continuation-in-part of PCT/US00/09054 filed Apr. 6, 2000 which is a continuation of U.S. patent application Ser. No. 09/288,461 filed Apr. 8, 1999 now issued U.S. Pat. No. 6,159,694.

FIELD OF THE INVENTION

This invention relates to compositions and methods for modulating expression of the human STAT3 gene, which encodes a naturally present DNA-binding protein involved in signal transduction and transcriptional activation, and is implicated in disease. This invention is also directed to methods for inhibiting STAT3-mediated signal transduction and transcriptional activation; these methods can be used diagnostically or therapeutically. Furthermore, this invention is directed to treatment of conditions associated with expression of the human STAT3 gene.

BACKGROUND OF THE INVENTION

The STAT (signal transducers and activators of transcription) family of proteins are DNA-binding proteins that play a dual role in signal transduction and activation of transcription. Presently, there are six distinct members of the STAT family (STAT1, STAT2, STAT3, STAT4, STAT5, and STAT6) and several isoforms (STAT1α, STAT1β, STAT3α and STAT3β). The activities of the STATs are modulated by various cytokines and mitogenic stimuli. Binding of a cytokine to its receptor results in the activation of Janus protein tyrosine kinases (JAKs) associated with these receptors. This in turn, phosphorylates STAT, resulting in translocation to the nucleus and transcriptional activation of STAT responsive genes. Phosphorylation on a specific tyrosine residue on the STATs results in their activation, resulting in the formation of homodimers and/or heterodimers of STAT which bind to specific gene promoter sequences. Events mediated by cytokines through STAT activation include cell proliferation and differentiation and prevention of apoptosis.

The specificity of STAT activation is due to specific cytokines, i.e. each STAT is responsive to a small number of specific cytokines. Other non-cytokine signaling molecules, such as growth factors, have also been found to activate STATs. Binding of these factors to a cell surface receptor associated with protein tyrosine kinase also results in phosphorylation of STAT.

STAT3 (also acute phase response factor (APRF)), in particular, has been found to be responsive to interleukin-6 (IL-6) as well as epidermal growth factor (EGF) (Darnell, Jr., J. E., et al., *Science*, 1994, 264, 1415–1421). In addition, STAT3 has been found to have an important role in signal transduction by interferons (Yang, C. -H., et al., *Proc. Natl. Acad. Sci. USA*, 1998, 95, 5568–5572). Evidence exists suggesting that STAT3 may be regulated by the MAPK pathway. ERK2 induces serine phosphorylation and also associates with STAT3 (Jain, N., et al., *Oncogene*, 1998, 17, 3157–3167).

STAT3 is expressed in most cell types (Zhong, Z., et al., *Proc. Natl. Acad. Sci. USA*, 1994, 91, 4806–4810). It induces the expression of genes involved in response to tissue injury and inflammation. STAT3 has also been shown to prevent apoptosis through the expression of bcl-2 (Fukada, T., et al., *Immunity*, 1996, 5, 449–460).

Aberrant expression of or constitutive expression of STAT3 is associated with a number of disease processes. STAT3 has been shown to be involved in cell transformation. It is constitutively activated in v-src-transformed cells (Yu, C. -L., et al., *Science*, 1995, 269, 81–83). Constitutively active STAT3 also induces STAT3 mediated gene expression and is required for cell transformation by src (Turkson, J., et al., *Mol. Cell. Biol.*, 1998, 18, 2545–2552). STAT3 is also constitutively active in Human T cell lymphotropic virus I (HTLV-I) transformed cells (Migone, T. -S. et al., *Science*, 1995, 269, 79–83).

Constitutive activation and/or overexpression of STAT3 appears to be involved in several forms of cancer, including myeloma, breast carcinomas, prostate cancer, brain tumors, head and neck carcinomas, melanoma, leukemias and lymphomas. Niu et al., *Cancer Res.*, 1999, 59, 5059–5063. Breast cancer cell lines that overexpress EGFR constitutively express phosphorylated STAT3 (Sartor, C. I., et al., *Cancer Res.*, 1997, 57, 978–987; Garcia, R., et al., *Cell Growth and Differentiation*, 1997, 8, 1267–1276). Activated STAT3 levels were also found to be elevated in low grade glioblastomas and medulloblastomas (Cattaneo, E., et al., *Anticancer Res.*, 1998, 18, 2381–2387).

Cells derived from both rat and human prostate cancers have been shown to have constitutively activated STAT3, with STAT3 activation being correlated with malignant potential. Expression of a dominant-negative STAT3 was found to significantly inhibit the growth of human prostate cells. Ni et al., *Cancer Res.*, 2000, 60, 1225–1228.

STAT3 has also been found to be constitutively activated in some acute leukemias (Gouilleux-Gruart, V., et al., *Leuk. Lymphoma*, 1997, 28, 83–88) and T cell lymphoma (Yu, C. -L., et al., *J. Immunol.*, 1997, 159, 5206–5210). Interestingly, STAT3 has been found to be constitutively phosphorylated on a serine residue in chronic lymphocytic leukemia (Frank, D. A., et al., *J. Clin. Invest.*, 1997, 100, 3140–3148).

STAT3 has been found to be constitutively active in myeloma tumor cells, both in culture and in bone marrow mononuclear cells from patients with multiple myeloma. These cells are resistant to Fas-mediated apoptosis and express high levels of Bcl-xL. STAT3 signaling was shown to be essential for survival of myeloma tumor cells by conferring resistance to apoptosis. Thus STAT3 is a potential target for therapeutic intervention in multiple myeloma and other cancers with activated STAT3 signaling. Catlett-Falcone, R., et al., *Immunity*, 1999, 10, 105–115. A gene therapy approach in a syngeneic mouse tumor model system has been used to inhibit activated STAT3 in vivo using a dominant-negative STAT3 variant. This inhibition of activated STAT3 signaling was found to suppress B16 melanoma tumor growth and induce apoptosis of B16 tumor cells in vivo. Interestingly, the number of apoptotic cells (95%) exceeded the number of transfected cells, indicating a possible antitumor "bystander effect" in which an inflammatory response (tumor infiltration by acute and chronic inflammatory cells) may participate in killing of residual tumor cells. Niu et al., *Cancer Res.*, 1999, 59, 5059–5063.

STAT3 may also play a role in inflammatory diseases including rheumatoid arthritis. Activated STAT3 has been found in the synovial fluid of rheumatoid arthritis patients (Sengupta, T. K., et al., *J. Exp. Med.*, 1995, 181, 1015–1025) and cells from inflamed joints (Wang, F., et al., *J. Exp. Med.*, 1995, 182, 1825–1831).

Multiple forms of STAT3 exist, generated by alternative splicing. STAT3β is a short form of STATS (also, STAT3α) that differs predominately by the absence of 55 amino acid residues at the C-terminus. This domain contains the transactivation domain, and thus, STAT3β may act as a negative regulator of STAT3 function (Caldenhoven, E., et al., *J. Biol. Chem.*, 1996, 271, 13221–13227). STAT3β has been found to be more stable and have greater DNA-binding activity than STAT3α, while STAT3α is more transcriptionally active.

There are currently several approaches for inhibiting STAT3 expression. U.S. Pat. Nos. 5,719,042 and 5,844,082 to Akira, S. and Kishimoto, T. disclose the use of inhibitors of APRF, including antibodies, antisense nucleic acids and ribozymes for the treatment of IL-6 associated diseases, such as inflammatory diseases, leukemia, and cancer. Schreiber, R. D., et al., in U.S. Pat. Nos. 5,731,155; 5,582,999; and 5,463,023, disclose methods of inhibiting transcriptional activation using short peptides that bind p91. Darnell, J. E., et al., in U.S. Pat. No. 5,716,622, disclose peptides containing the DNA binding domain of STATs, chimeric proteins containing the DNA binding domain, and antibodies to STATs for inhibiting STAT transcriptional activation.

The use of an antisense oligonucleotide targeted to the translation start region of human STAT3 has been disclosed (Grandis, J. R., et al., *J. Clin. Invest.*, 1998, 102, 1385–1392). In this report, a phosphorothioate oligodeoxynucleotide complementary to the translation start region of STAT3 inhibited TGF-α stimulated cell growth mediated by the epidermal growth factor receptor (EGFR).

There remains an unmet need for therapeutic compositions and methods targeting expression of STAT3, and disease processes associated therewith.

SUMMARY OF THE INVENTION

The present invention provides oligonucleotides which are targeted to nucleic acids encoding STAT3 and are capable of modulating STAT3 expression. The present invention also provides chimeric oligonucleotides targeted to nucleic acids encoding human STAT3. The oligonucleotides of the invention are believed to be useful both diagnostically and therapeutically, and are believed to be particularly useful in the methods of the present invention.

The present invention also comprises methods of modulating the expression of human STAT3, in cells and tissues, using the oligonucleotides of the invention. Methods of inhibiting STAT3 expression are provided; these methods are believed to be useful both therapeutically and diagnostically. These methods are also useful as tools, for example, for detecting and determining the role of STAT3 in various cell functions and physiological processes and conditions and for diagnosing conditions associated with expression of STAT3.

The present invention also comprises methods for diagnosing and treating inflammatory diseases, particularly rheumatoid arthritis, and cancers, including those of the breast, prostate, head and neck, and brain, myelomas and melanomas and leukemias and lymphomas. These methods are believed to be useful, for example, in diagnosing STAT3-associated disease progression. These methods employ the oligonucleotides of the invention. These methods are believed to be useful both therapeutically, including prophylactically, and as clinical research and diagnostic tools.

DETAILED DESCRIPTION OF THE INVENTION

STAT3 plays an important role in cytokine signal transduction. Overexpression and/or constitutive activation of STAT3 is associated with a number of inflammatory diseases and cancers. As such, this DNA-binding protein represents an attractive target for treatment of such diseases. In particular, modulation of the expression of STAT3 may be useful for the treatment of diseases such as rheumatoid arthritis, breast cancer, prostate cancer, brain cancer, head and neck cancer, myelomas, melanomas, leukemias and lymphomas.

The present invention employs antisense compounds, particularly oligonucleotides, for use in modulating the function of nucleic acid molecules encoding STAT3, ultimately modulating the amount of STAT3 produced. This is accomplished by providing oligonucleotides which specifically hybridize with nucleic acids, preferably mRNA, encoding STAT3.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding STAT3; in other words, a gene encoding STAT3, or mRNA expressed from the STAT3 gene. mRNA which encodes STAT3 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding STAT3, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of STAT3. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

In addition to the well known antisense effects of oligonucleotides, it has also been found that oligonucleotide analogs having at least one phosphorothioate bond can induce stimulation of a local immune response. This is described in U.S. Pat. No. 5,663,153 which is commonly assigned to the assignee of the present invention and is herein incorporated by reference in its entirety. This immunostimulatory effect does not appear to be related to any antisense effect which these oligonucleotide analogs may or may not possess. These oligonucleotide analogs are useful as immunopotentiators, either alone or in combination with other therapeutic modalities, such as drugs, particularly antiinfective and anticancer drugs, and surgical procedures to increase efficacy. In addition, the antiinfective and anticancer effects already possessed by certain antisense oligonucleotide analogs are enhanced through such immune stimulation.

It has also been found that oligonucleotide analogs having at least one phosphorothioate bond can be used to induce stimulation of a systemic or humoral immune response. Thus, these oligonucleotides are also useful as immunopotentiators of an antibody response, either alone or in combination with other therapeutic modalities. U.S. Pat. No. 5,663,153.

It is presently believed, therefore, that, in addition to the antisense effects of oligonucleotides targeted to STAT3, oligonucleotides containing at least one phosphorothioate backbone linkage may be useful in eliciting an immune response which may add to the antitumor "bystander effect"

already observed with dominant negative inhibitors of STAT3 signaling. Niu et al., *Cancer Res.,* 1999, 59, 5059–5063. This effect is believed to be related to tumor infiltration by acute and chronic inflammatory cells which may participate in killing of residual tumor cells. Thus the therapeutic effects of antisense oligonucleotides targeted to STAT3 may be potentiated by the immunostimulatory properties of the oligonucleotides themselves. Alternatively, oligonucleotides which may not be targeted to STAT3 but which contain at least one phosphorothioate backbone linkage may be used as adjuvants in combination with antisense or other inhibitors of STAT3.

The oligonucleotides of this invention can be used in diagnostics, therapeutics, prophylaxis, and as research reagents and in kits. Since the oligonucleotides of this invention hybridize to nucleic acids encoding STAT3, sandwich, calorimetric and other assays can easily be constructed to exploit this fact. Provision of means for detecting hybridization of oligonucleotide with the STAT3 gene or mRNA can routinely be accomplished. Such provision may include enzyme conjugation, radiolabelling or any other suitable detection systems. Kits for detecting the presence or absence of STAT3 may also be prepared.

The present invention is also suitable for diagnosing abnormal inflammatory states or certain cancers in tissue or other samples from patients suspected of having an inflammatory disease such as rheumatoid arthritis or cancers such as breast, brain, or head and neck cancer, melanomas, myelomas, leukemias and lymphomas. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2=, 3= or 5= hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3= to 5= phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3=-alkylene phosphonates and chiral phosphonates, phosphinates, phosphoramidates including 3=-amino phosphoramidate and aminoalkylphosphoramidates, thionophosphoramidates, thionoalkylphosphonates, thionoalkylphosphotriesters, and boranophosphates having normal 3=–5= linkages, 2=–5= linked analogs of these, and those having inverted polarity wherein the adjacent pairs of nucleoside units are linked 3=–5= to 5=–3= or 2=–5= to 5=–2=. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677;

5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_2$ON(CH$_3$)$_2$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2= position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta* 1995, 78, 486–504) i.e., an alkoxyalkoxy group. A further preferred modification includes 2=-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples hereinbelow.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2=–5= linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc.*

*Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. APharmaceutically acceptable salts@ are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a Aprodrug@ form. The term Aprodrug@ indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: Goodman & Gilman's *The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.).

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (*J. Med. Chem.* 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-a-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (*Helv. Chim. Acta* 1995, 78, 486–506). For ease of synthesis, the last nucleotide may be a deoxynucleotide. 2'-O—CH$_2$CH$_2$OCH$_3$-cytosines may be 5-methyl cytosines.

Synthesis of 5-Methyl Cytosine Monomers 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gun was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M) tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–260?C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$C$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated Nacl. The water layers wore back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled, to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overniqht in a cold room. Salts were filtered from the reaction mixture and the solution was evaporated. The residue was dissolved in EtOAc (1 L) and the insoluble solids wore removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxytetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAcHexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling Va. or ChemGenes, Needham Mass.).

2=-O-(dimethylaminooxyethyl) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy)ethyl]-5-methyluridine as white foam (1.95, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages are synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (*Science* 1991, 254, 1497–1500).

After cleavage from the controlled pore glass column (Applied Biosystems) and deblocking in concentrated ammonium hydroxide at 55?C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels or capillary gel electrophoresis and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Alternatively, oligonucleotides were synthesized in 96 well plate format via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-di-isopropyl phosphoramidites were purchased from commercial vendors (e.g. PE-Applied Biosystems, Foster City, Calif., or Pharmacia, Piscataway, N.J.). Non-standard nucleosides are synthesized as per published methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 2

Human STAT3 Oligodeoxynucleotide Sequences

Antisense oligonucleotides were designed to target human STAT3. Target sequence data are from the APRF cDNA sequence published by Akira, S. et al. (*Cell*, 1994, 77, 63–71); Genbank accession number L29277, provided herein as SEQ ID NO: 1. A set of oligodeoxynucleotides were synthesized with phosphorothioate linkages. 2'-deoxy cytosines were 5-methyl cytosines. These oligonucleotide sequences are shown in Table 1. An additional set of oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines and 2'-deoxy cytosines were 5-methyl-cytosines. These oligonucleotide sequences are shown in Table 2.

An appropriate cell line, typically expressing high levels of STAT3, is chosen for in vitro studies. Cell culture conditions are those standard for that particular cell line. Oligonucleotide treatment is for four hours and mRNA usually isolated 24 to 48 hours following initial treatment.

mRNA is isolated using the RNAEASY7 kit (Qiagen, Santa Clarita, Calif.).

TABLE 1

Nucleotide Sequences of Human STAT3 Phosphorothioate Oligodeoxynucleotides

| ISIS NO. | NUCLEOTIDE SEQUENCE[1] (5' ->3') | SEQ ID NO: | TARGET GENE NUCLEOTIDE CO-ORDINATES[2] | GENE TARGET REGION |
|---|---|---|---|---|
| 106691 | GTCTGCGCCGCCGCCCCGAA | 2 | 0010-0029 | 5'-UTR |
| 106692 | GGCCGAAGGGCCTCTCCGAG | 3 | 0130-0149 | 5'-UTR |
| 106693 | TCCTGTTTCTCCGGCAGAGG | 4 | 0202-0221 | AUG |
| 106694 | CATCCTGTTTCTCCGGCAGA | 5 | 0204-0223 | AUG |
| 106695 | GCCATCCTGTTTCTCCGGCA | 6 | 0206-0225 | AUG |
| 106696 | GGGCCATCCTGTTTCTCCGG | 7 | 0208-0227 | AUG |
| 106697 | TTGGGCCATCCTGTTTCTCC | 8 | 0210-0229 | AUG |
| 106698 | CATTGGGCCATCCTGTTTCT | 9 | 0212-0231 | AUG |
| 106699 | TCCATTGGGCCATCCTGTTT | 10 | 0214-0233 | AUG |
| 106700 | ATTCCATTGGGCCATCCTGT | 11 | 0216-0235 | AUG |
| 106701 | TGATTCCATTGGGCCATCCT | 12 | 0218-0237 | AUG |
| 106702 | GCTGATTCCATTGGGCCATC | 13 | 0220-0239 | AUG |
| 106703 | TAGCTGATTCCATTGGGCCA | 14 | 0222-0241 | AUG |
| 106704 | TGTAGCTGATTCCATTGGGC | 15 | 0224-0243 | coding |
| 106705 | CTGTAGAGCTGATGGAGCTG | 16 | 0269-0288 | coding |
| 106706 | CCCAATCTTGACTCTCAATC | 17 | 0331-0350 | coding |
| 106707 | CCCAGGAGATTATGAAACAC | 18 | 0386-0405 | coding |
| 106708 | ACATTCGACTCTTGCAGGAA | 19 | 0431-0450 | coding |
| 106709 | TCTGAAGAAACTGCTTGATT | 20 | 0475-0494 | coding |
| 106710 | GGCCACAATCCGGGCAATCT | 21 | 0519-0538 | coding |
| 106711 | TGGCTGCAGTCTGTAGAAGG | 22 | 0562-0581 | coding |
| 106712 | CTGCTCCAGCATCTGCTGCT | 23 | 0639-0658 | coding |
| 106713 | TTTCTGTTCTAGATCCTGCA | 24 | 0684-0703 | coding |
| 106714 | TAGTTGAAATCAAAGTCATC | 25 | 0728-0747 | coding |
| 106715 | TTCCATTCAGATCTTGCATG | 26 | 0772-0791 | coding |
| 106716 | TCTGTTCCAGCTGCTGCATC | 27 | 0817-0836 | coding |
| 106717 | TCACTCACGATGCTTCTCCG | 28 | 0860-0879 | coding |
| 106718 | GAGTTTTCTGCACGTACTCC | 29 | 0904-0923 | coding |
| 106719 | ATCTGTTGCCGCCTCTTCCA | 30 | 0947-0968 | coding |
| 106720 | CTAGCCGATCTAGGCAGATG | 31 | 0991-1010 | coding |
| 106721 | CGGGTCTGAAGTTGAGATTC | 32 | 1034-1053 | coding |
| 106722 | CGGCCGGTGCTGTACAATGG | 33 | 1110-1129 | coding |
| 106723 | TTTCATTAAGTTTCTGAACA | 34 | 1155-1174 | coding |
| 106724 | AGGATGCATGGGCATGCAGG | 35 | 1200-1219 | coding |
| 106725 | GACCAGCAACCTGACTTTAG | 36 | 1260-1279 | coding |
| 106726 | ATGCACACTTTAATTTTAAG | 37 | 1304-1323 | coding |
| 106727 | TTCCGGGATCCTCTGAGAGC | 38 | 1349-1368 | coding |
| 106728 | TTCCATGTTCATCACTTTTG | 39 | 1392-1411 | coding |
| 106729 | GTCAAGTGTTTGAATTCTGC | 40 | 1436-1455 | coding |
| 106730 | CAATCAGGAAGCATCACAA | 41 | 1495-1514 | coding |
| 106731 | TACACCTCGGTCTCAAAGGT | 42 | 1538-1557 | coding |
| 106732 | TGACAAGGAGTGGGTCTCTA | 43 | 1581-1600 | coding |
| 106733 | CGCCCAGGCATTTGGCATCT | 44 | 1626-1645 | coding |
| 106734 | CATTCTTGGGATTGTTGGTC | 45 | 1669-1688 | coding |
| 106735 | CACTTGGTCCCAGGTTCCAA | 46 | 1713-1732 | coding |
| 106736 | CCCGCTTGGTGGTGGACGAG | 47 | 1756-1775 | coding |
| 106737 | AGTTCACACCAGGCCCTAGG | 48 | 1816-1835 | coding |
| 106738 | GTTTTCTTTGCAGAAGTTAG | 49 | 1860-1879 | coding |
| 106739 | ATATTGTCTAGCCAGACCCA | 50 | 1904-1923 | coding |
| 106740 | AACCCATGATGTACCCTTCA | 51 | 1963-1982 | coding |
| 106741 | GCTTAGTGCTCAAGATGGCC | 52 | 2005-2024 | coding |
| 106742 | GCTGCTTTCACTGAAGCGCA | 53 | 2043-2062 | coding |
| 106743 | GTGAAAGTGACGCCTCCTTC | 54 | 2066-2085 | coding |
| 106744 | CTGATGTCCTTCTCCACCCA | 55 | 2087-2106 | coding |
| 106745 | ACTGGATCTGGGTCTTACCG | 56 | 2107-2126 | coding |
| 106746 | AAATGACATGTTGTTCAGCT | 57 | 2151-2170 | coding |
| 106747 | GCCCATGATGATTTCAGCAA | 58 | 2169-2188 | coding |
| 106748 | TATTGGTAGCATCCATGATC | 59 | 2194-2213 | coding |
| 106749 | ATAGACAAGTGGACACAACA | 60 | 2217-2236 | coding |
| 106750 | TTGGGAATGTCAGGATAGAO | 61 | 2237-2256 | coding |
| 106751 | CTCCTGGCTCTCTGGCCGAC | 62 | 2280-2299 | coding |
| 106752 | ACCTOGGTCAGCTTCAGGAT | 63 | 2301-2320 | coding |
| 106753 | CACAGATAAACTTGGTCTTC | 64 | 2338-2357 | coding |
| 106754 | ATCGGCAGGTCAATGGTATT | 65 | 2378-2397 | coding |
| 106755 | CCAAACTGCATCAATGAATC | 66 | 2414-2433 | coding |
| 106756 | GGTTCAGCACCTTCACCATT | 67 | 2438-2457 | coding |
| 106757 | GAGGGACTCAAACTGCCCTC | 68 | 2466-2485 | coding |
| 106758 | CAACTCCATGTCAAAGGTGA | 69 | 2484-2503 | coding |

TABLE 1-continued

Nucleotide Sequences of Human STAT3 Phosphorothioate Oligodeoxynucleotides

| ISIS NO. | NUCLEOTIDE SEQUENCE[1] (5'->3') | SEQ ID NO: | TARGET GENE NUCLEOTIDE CO-ORDINATES[2] | GENE TARGET REGION |
|---|---|---|---|---|
| 106759 | TTCTCAGCTCCTCACATGGG | 70 | 2525-2544 | STOP |
| 106760 | CGTTCTCAGCTCCTCACATG | 71 | 2527-2546 | STOP |
| 106761 | TCCGTTCTCAGCTCCTCACA | 72 | 2529-2548 | STOP |
| 106762 | CTTCCGTTCTCAGCTCCTCA | 73 | 2531-2550 | STOP |
| 106763 | AGCTTCCGTTCTCAGCTCCT | 74 | 2533-2552 | STOP |
| 106764 | AGAATGCAGGTAGGCGCCTC | 75 | 2569-2588 | 3'-UTR |
| 106765 | ACCACAAAGTTAGTAGTTTC | 76 | 2623-2642 | 3'-UTR |
| 106766 | TGCTCAAAGATAGCAGAAGT | 77 | 2665-2684 | 3'-UTR |
| 106767 | ATTCACTCATTTCTCTATTT | 78 | 2701-2720 | 3'-UTR |
| 106768 | CATTTAGATAAAAGCAGATC | 79 | 2727-2746 | 3'-UTR |
| 106769 | ACATCCTTATTTGCATTTAG | 80 | 2740-2759 | 3'-UTR |
| 106770 | GATCATGGGTCTCAGAGAAC | 81 | 2760-2779 | 3'-UTR |

"C" residues are 5-methyl-cytosines; all linkages are phosphorothioate linkages.
2 Coordinates from Genbank Accession No. L29277, locus name "HUMAPRF", SEQ ID NO. 1.

TABLE 2

Nucleotide Sequences of Human STAT3 Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 106771 | GTCTGCGCCGCCGCCCCGAA | 2 | 0010-0029 | 5'-UTR |
| 106772 | GGCCGAAGGGCCTCTCCGAG | 3 | 0130-0149 | 5'-UTR |
| 106773 | TCCTGTTTCTCCGGCAGAGG | 4 | 0202-0221 | AUG |
| 106774 | CATCCTGTTTCTCCGGCAGA | 5 | 0204-0223 | AUG |
| 106775 | GCCATCCTGTTTCTCCGGCA | 6 | 0206-0225 | AUG |
| 106776 | GGGCCATCCTGTTTCTCCGG | 7 | 0208-0227 | AUG |
| 106777 | TTGGGCCATCCTGTTTCTCC | 8 | 0210-0229 | AUG |
| 106778 | CATTGGGCCATCCTGTTTCT | 9 | 0212-0231 | AUG |
| 106779 | TCCATTGGGCCATCCTGTTT | 10 | 0214-0233 | AUG |
| 106780 | ATTCCATTGGGCCATCCTGT | 11 | 0216-0235 | AUG |
| 106781 | TGATTCCATTGGGCCATCCT | 12 | 0218-0237 | AUG |
| 106782 | GCTGATTCCATTGGGCCATC | 13 | 0220-0239 | AUG |
| 106783 | TAGCTGATTCCATTGGGCCA | 14 | 0222-0241 | AUG |
| 106784 | TGTAGCTGATTCCATTGGGC | 15 | 0224-0243 | coding |
| 106785 | CTGTAGACTGATGGAGCTG | 16 | 0269-0288 | coding |
| 106786 | CCCAATCTTGACTCTCAATC | 17 | 0331-0350 | coding |
| 106787 | CCCAGGAGATTATGAAACAC | 18 | 0386-0405 | coding |
| 106788 | ACATTCGACTCTTGCAGGAA | 19 | 0431-0450 | coding |
| 106789 | TCTGAAGAAACTGCTTGATT | 20 | 0475-0494 | coding |
| 106790 | GGCCACAATCCGGGCAATCT | 21 | 0519-0538 | coding |
| 106791 | TGGCTGCAGTCTGTAGAAGG | 22 | 0562-0581 | coding |
| 106792 | CTGCTCCAGCATCTGCTGCT | 23 | 0639-0658 | coding |
| 106793 | TTTCTGTTCTAGATCCTGCA | 24 | 0684-0703 | coding |
| 106794 | TAGTTGAAATCAAAGTCATC | 25 | 0728-0747 | coding |
| 106795 | TTCCATTCAGATCTTGCATG | 26 | 0772-0791 | coding |
| 106796 | TCTGTTCCAGCTGCTGCATC | 27 | 0817-0836 | coding |
| 106797 | TCACTCACGATGCTTCTCCG | 28 | 0860-0879 | coding |
| 106798 | GAGTTTTCTGCACGTACTCC | 29 | 0904-0923 | coding |
| 106799 | ATCGTTGCCGCCTCTTCCA | 30 | 0947-0968 | coding |
| 106800 | CTAGCCGATCTAGGCAGATG | 31 | 0991-1010 | coding |
| 106801 | CGGGTCTGAAGTTGAGATTC | 32 | 1034-1053 | coding |
| 106802 | CGGCCGGTGCTGTACAATGG | 33 | 1110-1129 | coding |
| 106803 | TTTCATTAAGTTTCTGAACA | 34 | 1155-1174 | coding |
| 106804 | AGGATGCATGGGCATGCAGG | 35 | 1200-1219 | coding |
| 106805 | GACCAGCAACCTGACTTTAG | 36 | 1260-1279 | coding |
| 106806 | ATGCACACTTTAATTTTAAG | 37 | 1304-1323 | coding |
| 106807 | TTCCGGGATCCTCTGAGAGC | 38 | 1349-1368 | coding |
| 106808 | TTCCATGTTCATCACTTTTG | 39 | 1392-1411 | coding |
| 106809 | GTCAAGTGTTTGAATTCTGC | 40 | 1436-1455 | coding |
| 106810 | CAATCAGGGAAGCATCACAA | 41 | 1495-1514 | coding |
| 106811 | TACACCTCGGTCTCAAAGGT | 42 | 1538-1557 | coding |
| 106812 | TGACAAGGAGTGGGTCTCTA | 43 | 1581-1600 | coding |
| 106813 | CGCCCAGGCATTTGGCATCT | 44 | 1626-1645 | coding |
| 106814 | CATTCTTGGGATTGTTGGTC | 45 | 1669-1688 | coding |
| 106815 | CACTTGGTCCCAGGTTCCAA | 46 | 1713-1732 | coding |
| 106816 | CCCGCTTGGTGGTGGACGAG | 47 | 1756-1775 | coding |
| 106817 | AGTTCACACCAGGCCCTAGG | 48 | 1816-1835 | coding |
| 106818 | GTTTTCTTTGCAGAAGTTAG | 49 | 1860-1879 | coding |
| 106819 | ATATTGTCTAGCCAGACCCA | 50 | 1904-1923 | coding |
| 106820 | AACCCATGATGTACCCTTCA | 51 | 1963-1982 | coding |
| 106821 | GCTTAGTGCTCAAGATGGCC | 52 | 2005-2024 | coding |
| 106822 | GCTGCTTTCACTGAAGCGCA | 53 | 2043-2062 | coding |
| 106823 | GTGAAAGTGACGCCTCCTTC | 54 | 2066-2085 | coding |
| 106824 | CTGATGTCCTTCTCCACCCA | 55 | 2087-2106 | coding |
| 106825 | ACTGGATCTGGGTCTTACCG | 56 | 2107-2126 | coding |
| 106826 | AAATGACATGTTGTTCAGCT | 57 | 2151-2170 | coding |
| 106827 | GCCCATGATGATTTCAGCAA | 58 | 2169-2188 | coding |
| 106828 | TATTGGTAGCATCCATGATC | 59 | 2194-2213 | coding |
| 106829 | ATAGACAAGTGGAGACAACA | 60 | 2217-2236 | coding |
| 106830 | TTGGGAATGTCAGGATAGAG | 61 | 2237-2256 | coding |
| 106831 | CTCCTGGCTCTCTGGCCGAC | 62 | 2280-2299 | coding |
| 106832 | ACCTGGGTCAGCTTCAGGAT | 63 | 2301-2320 | coding |
| 106833 | CACAGATAAACTTGGTCTTC | 64 | 2338-2357 | coding |
| 106834 | ATCGGCAGGTCAATGGTATT | 65 | 2378-2397 | coding |
| 106835 | CCAAACTGCATCAATGAATC | 66 | 2414-2433 | coding |
| 106836 | GGTTCAGCACCTTCACCATT | 67 | 2438-2457 | coding |
| 106837 | GAGGGACTCAAACTGCCCTC | 68 | 2466-2485 | coding |
| 106838 | CAACTCCATGTCAAAGGTGA | 69 | 2484-2503 | coding |
| 106839 | TTCTCAGCTCCTCACATGGG | 70 | 2525-2544 | STOP |
| 106840 | CGTTCTCAGCTCCTCACATG | 71 | 2527-2546 | STOP |
| 106841 | TCCGTTCTCAGCTCCTCACA | 72 | 2529-2548 | STOP |
| 106842 | CTTCCGTTCTCAGCTCCTCA | 73 | 2531-2550 | STOP |
| 106843 | AGCTTCCGTTCTCAGCTCCT | 74 | 2533-2552 | STOP |
| 106844 | AGAATGCAGGTAGGCGCCTC | 75 | 2569-2588 | 3'-UTR |
| 106845 | ACCACAAAGTTAGTAGTTTC | 76 | 2623-2642 | 3'-UTR |
| 106846 | TGCTCAAAGATAGCAGAAGT | 77 | 2665-2684 | 3'-UTR |
| 106847 | ATTCACTCATTTCTCTATTT | 78 | 2701-2720 | 3'-UTR |
| 106848 | CATTTAGATAAAAGCAGATC | 79 | 2727-2746 | 3'-UTR |
| 106849 | ACATCCTTATTTGCATTTAG | 80 | 2740-2759 | 3'-UTR |
| 106850 | GATCATGGGTCTCAGAGAAC | 81 | 2760-2779 | 3'-UTR |

[1]Emboldened residues are 2'-methoxyethoxy residues, 2'-methoxyethoxy cytosine residues and 2'-OH cytosine residues are 5-methyl-cytosines; all linkages are phosphorothioate linkages.
[2]Coordinates from Genbank Accession No. L29277, locus name "HUMAPRE", SEQ ID NO. 1.

Oligonucleotide activity is assayed by quantitation of STAT3 mRNA levels by real-time PCR (RT-PCR) using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in RT-PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

RT-PCR reagents are obtained from PE-Applied Biosystems, Foster City, Calif. RT-PCR reactions are carried out by adding 25 ?l PCR cocktail (1×TAQMAN7 buffer A, 5.5 mM MgCl$_2$, 300 μM each of dATP, dCTP and dGTF, 600 μM of dUTP, 100 nM each of forward primer, reverse primer, and probe, 20 U RNAse inhibitor, 1.25 units AMPLITAQ GOLD7, and 12.5 U MuLV reverse transcriptase) to 96 well plates containing 25 μl poly(A) mRNA solution. The RT reaction is carried out by incubation for 30 minutes at 48° C. following a 10 minute incubation at 95° C. to activate the AMPLITAQ GOLD7, 40 cycles of a two-step PCR protocol are carried out: 95° C. for 15 seconds (denaturation) followed by 60° C. for 1.5 minutes (annealing/extension).

STAT3 PCR primers and a probe can be designed using commercial software (e.g. Oligo 5.0).

Example 3

Mouse STAT3 Oligonucleotide Sequences

Antisense oligonucleotides were designed to target mouse STAT3. Target sequence data are from the STAT3 cDNA sequence submitted by Zhong, Z.; Genbank accession number U06922, provided herein as SEQ ID NO: 82. Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines were 5-methyl-cytosines. Oligonucleotide sequences are shown in Table 3.

The B lymphoma cell line, BCL1 was obtained from ATCC (Rockville, Md.). BCL1 cells were cultured in RPMI 1640 medium.

BCL1 cells (5×10$^6$ cells in PBS) were transfected with oligonucleoulides by electroporation, at 200 V, 1000 μF using a BTX Electro Cell Manipulator 600 (Genetronics, San Diego, Calif.). For an initial screen, BCL1 were electroporated with 10 μM oligonucleotide and RNA collected 24 hours later. Controls without oligonucleotide were subjected to the same electroporation conditions.

Total cellular RNA was isolated using the RNEASY7 kit (Qiagen, Santa Clarita, Calif.). RNAse protection experiments were conducted using RIBOQUANT™ kits and template sets according to the manufacturer's instructions (Pharmingen, San Diego, Calif.). Northern blotting was performed as described in Chiang, M-Y. et al. (*J. Biol. Chem.*, 1991, 266, 18162–18171), using a rat cDNA probe prepared by Xho I/Sal I restriction digest of psvsport-1 plasmid (ATCC, Rockville, Md.). mRNA levels were quantitated using a PhosphorImager (Molecular Dynamics, Sunnyvale, Calif.).

TABLE 3

Nucleotide Sequences of Mouse STAT3 Chimeric (deoxy gapped) Phosphorothioate Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17136 | GTTCCACTGAGCCATCCTGC | 83 | 0064-0083 | AUG |
| 17137 | TTCAGGTAGCGTGTGTCCAG | 84 | 0096-0115 | coding |
| 17138 | ATGTGACTCTTTGCTGGCTG | 85 | 0205-0224 | coding |
| 17139 | CCAAGAGATTATGAAACACC | 86 | 0233-0252 | coding |
| 17140 | GCTCCAACATCTGCTGCTTC | 87 | 0485-0504 | coding |
| 17141 | GCTCTTCATCAGTCAGTGTC | 88 | 0767-0786 | coding |
| 17142 | ATCTGACACCCTGAGTAGTT | 89 | 1680-1699 | coding |
| 17143 | GCCAGACCCAGAAGGAGAAG | 90 | 1742-1761 | coding |
| 17144 | CGCTCCTTGCTGATGAAACC | 91 | 1827-1846 | coding |
| 17145 | AACTTGGTCTTCAGGTACGG | 92 | 2178-2197 | coding |
| 17146 | ATCAATGAATCTAAAGTGCG | 93 | 2253-2272 | coding |
| 17147 | TCAGCACCTTCACCGTTATT | 94 | 2283-2302 | coding |
| 17148 | ACTCAAACTGCCCTCCTGCT | 95 | 2309-2328 | coding |
| 17149 | GGTTTCAGCTCCTCACATGG | 96 | 2374-2393 | STOP |
| 17150 | TAAAAAAAAAAATCTGGAAC | 97 | 2485-2504 | 3'-UTR |
| 17151 | AAGATAGCAGAAGTAGGAAA | 98 | 2506-2525 | 3'-UTR |
| 17152 | AAAAAGTGCCCAGATTGCCC | 99 | 2527-2546 | 3'-UTR |
| 17153 | ATCACCCACACTCACTCATT | 100 | 2557-2645 | 3'-UTR |
| 17154 | CCTTTGCCTCCCTTCTGCTC | 101 | 2626-2645 | 3'-UTR |
| 17155 | TGAAAAAGGAGGGCAGGCGG | 102 | 2665-2684 | 3'-UTR |
| 17156 | CACCAGGAGGCACTTGTCTA | 103 | 2705-2724 | 3'-UTR |
| 17157 | AACCTCCTGGGCTTAGTCCT | 104 | 2822-2841 | 3'-UTR |
| 23176 | AAAAAGTGCGCAGATTGCCC | 105 | 1 base mismatch control | |
| 23177 | AAAAAGTCCGCTGATTGCCC | 106 | 3 base mismatch control | |
| 23178 | AAAAACTCCGCTGAATGCCC | 107 | 5 base mismatch control | |

[1]All 2'-MOE cytosine residues are 5-methyl-cytosines; all linkages are phosphorothioate linkages.
[2]Co-ordinates from Genbank Accession No. U06922, locus name "MMU06922", SEQ ID NO. 82.

Results are shown in Table 4. Oligonucleotides 17138 (SEQ ID NO. 85), 17139 (SEQ ID NO. 86), 17140 (SEQ ID NO. 87), 17143 (SEQ ID NO. 90), 17144 (SEQ ID NO. 91), 17152 (SEQ ID NO. 99), 17153 (SEQ ID NO. 100), 17156 (SEQ ID NO. 103), and 17157 (SEQ ID NO. 104) gave better than 45% inhibition in this assay.

TABLE 4

Inhibition of Mouse STAT3 mRNA expression in BCL1 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 17136 | 83 | AUG | 75% | 25% |
| 17137 | 84 | coding | 75% | 25% |
| 17138 | 85 | coding | 37% | 63% |
| 17139 | 86 | coding | 41% | 59% |
| 17140 | 87 | coding | 40% | 60% |
| 17141 | 88 | coding | 62% | 38% |
| 17142 | 89 | coding | 70% | 30% |
| 17143 | 90 | coding | 42% | 58% |
| 17144 | 91 | coding | 55% | 45% |
| 17145 | 92 | coding | 89% | 11% |
| 17146 | 93 | coding | 91% | 9% |
| 17147 | 94 | coding | 70% | 30% |
| 17148 | 95 | coding | 69% | 31% |

TABLE 4-continued

Inhibition of Mouse STAT3 mRNA expression in BCL1 Cells by
Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| 17149 | 96  | STOP   | 70% | 30% |
| 17150 | 97  | 3'-UTR | 95% | 5%  |
| 17151 | 98  | 3'-UTR | 92% | 8%  |
| 17152 | 99  | 3'-UTR | 25% | 75% |
| 17153 | 100 | 3'-UTR | 44% | 56% |
| 17154 | 101 | 3'-UTR | 80% | 20% |
| 17155 | 102 | 3'-UTR | 78% | 22% |
| 17156 | 103 | 3'-UTR | 40% | 60% |
| 17157 | 104 | 3'-UTR | 53% | 47% |

Example 4

Dose Response of Antisense Chimeric (Deoxy Gapped) Phosphorothioate Oligonucleotide Effects on Mouse STAT3 Protein Levels in BCL1 Cells ISIS 17152 (SEQ ID. NO. 99) was chosen for further study. The effect of this oligonucleotide on protein levels was determined by Western blot. ISIS 23177 (SEQ ID NO. 106), a 3 base mismatch, was used as a control. BCL1 cells were grown, treated and processed as described in Example 2.

Nuclear extracts from primary B cells and B lymphoma cell lines were prepared as described in Karras, J. G., et al. (*J. Exp. Med.*, 1997, 185, 1035–1042).

Western blotting was performed as described in Karras, J. G. et al. (*J. Immunol.*, 1996, 157, 2299). STAT1 and STAT3 antibodies were obtained from UBI (Lake Placid, N.Y.).

Results are shown in Table 5. ISIS 17152 (SEQ ID NO. 99) was significantly better at reducing STAT3 protein levels than the mismatch control.

TABLE 5

Dose Response of BCL1 cells to STAT3
Chimeric (deoxy gapped) Phosphorothioate Oligonucleotides

| ISIS # | SEQ ID NO: | ASO Gene Target | Dose | % protein Expression | % protein Inhibition |
|---|---|---|---|---|---|
| control | — | — | — | 100% | — |
| 17152 | 99 | 3'-UTR | 10 nM | 41.7% | 58.3% |
| " | " | " | 15 nM | 42.5% | 57.5% |
| " | " | " | 20 nM | 26.5% | 73.5% |
| 23177 | 106 | control | 10 nM | 75.1% | 24.9% |
| " | " | " | 15 nM | 67.6% | 32.4% |
| " | " | " | 20 nM | 62.6% | 37.4% |

Example 5

Inhibition of BCL1 Proliferation by STAT3 Antisense Chimeric (Deoxy Gapped) Phosphorothioate Oligonucleotide The effect of ISIS 17152 (SEQ ID NO. 99) on BCL1 proliferation was determined. BCL1 cells contain constitutively active STAT3 which is thought to be responsible for their proliferation. BCL1 cells were grown, treated and processed as described in Example 2.

$1\times10^5$ BCL1 cells were incubated in 96-well plates in 200 µL complete RPMI following electroporation. Cultures were pulsed with 1 µCi of [$^3$H]-thymidine for the last 8 hours of culture and cells were harvested and analyzed for thymidine incorporation as described in Francis, D. A. et al. (*Int. Immunol.*, 1995, 7, 151–161) 48 hours after electroporation.

Results are shown in Table 6. ISIS 17152 (SEQ ID NO. 99) was able to reduce BCL1 cell proliferation by approximately 50% whereas the mismatch control had no effect.

TABLE 6

Inhibition of BCL1 Cell Proliferation with STAT3
Chimeric (deoxy gapped) Phosphorothioate Oligonucleotides

| ISIS # | SEQ ID NO: | ASO Gene Target | Dose | % Cell Proliferation | % Cell Inhibition |
|---|---|---|---|---|---|
| control | — | — | — | 100% | — |
| 17152 | 99 | 3'-UTR | 10 nM | 78.5% | 21.5% |
| " | " | " | 15 nM | 54.4% | 45.6% |
| " | " | " | 20 nM | 50.2% | 49.8% |
| 23177 | 106 | control | 10 nM | 117.0% | — |
| " | " | " | 15 nM | 99.7% | 0.3% |
| " | " | " | 20 nM | 107.0% | — |

Example 6

Inhibition of BCL1 IgM Secretion by STAT3 Antisense Chimeric (Deoxy Gapped) Phosphorothioate Oligonucleotides The effect of ISIS 17152 (SEQ ID. NO. 99) on IgM secretion levels was determined. STAT3 has been implicated in regulation of IgM expression (Faris, M., et al., *Immunology*, 1997, 90, 350–357). BCL1 cells were grown, treated and processed as described in Example 2.

$1\times10^6$ BCL1 cells were incubated in 12-well plates in 2 mL complete RPMI following electroporation. Supernatant was replaced at 24 hour post electroporation with fresh medium. 48 hours later, supernatants were harvested, centrifuged to remove cells, and assayed for IgM content using the OPT-EIA™ ELISA kit (Pharmingen, San Diego, Calif.) and capture and detecting antibodies for mouse IgM (Southern Biotechnology, Birmingham, Ala.).

Results are shown in Table 7. ISIS 17152 (SEQ ID NO. 99) was significantly better at reducing IgM secretion than the mismatch control.

TABLE 7

Inhibition of BCL1 IgM secretion by STAT3
Chimeric (deoxy gapped) Phosphorothioate Oligonucleotides

| ISIS # | SEQ ID NO: | ASO Gene Target | Dose | % IgM Expression | % IgM Inhibition |
|---|---|---|---|---|---|
| control | — | — | — | 100% | — |
| 17152 | 99 | 3'-UTR | 5 nM | 34.2% | 65.8% |
| " | " | " | 15 nM | 23.1% | 76.9% |
| 23177 | 106 | control | 5 nM | 110.0% | — |
| " | " | " | 15 nM | 80.8% | 19.2% |

Example 7

Induction of Chemokines in BCL1 Cells Following Treatment with STAT3 Antisense Chimeric (Deoxy Gapped) Phosphorothioate Oligonucleotide The effect of ISIS 17152 (SEQ ID. NO. 99) on chemokine levels was determined. BCL1 cells were grown, treated and processed as described in Example 2. Chemokine gene expression was induced in BCL1 cells by addition of 10 µM at a CpG-containing oligonucleotide to the media 16 hours following antisense oligonucleotide electroporation. CpG-containing oligonucleotides are immune-stimulatory (Krieg, A. M., et al., *Nature*, 1995, 374, 546–549). The levels of chemokines were measured eight hours later using RNase protection assay as described in Example 2 with a mouse chemokine template set, Mck-5 (Pharmingen, San Diego, CA).

Results are shown in Table 8. ISIS 17152 (SEQ ID. NO. 99) was able to induce the expression of the chemokines, RANTES, MIP-1α and MIP-1β whereas the mismatch control had minimal effect.

TABLE 8

Induction of Chemokines in BCL1 Cells Following Treatment with STAT3 Chimeric (deoxy gapped) Phosphorothioate Oligonucleotides

| ISIS # | SEQ ID NO: | ASO Gene Target | Dose | % RANTES mRNA | % MIP1a mRNA | % MIP1b mRNA |
|---|---|---|---|---|---|---|
| control | " | " | " | 100% | 100% | 100% |
| 17152 | 99 | 3'-UTR | 5 nM | 236% | 201% | 133% |
| " | " | " | 10 nM | 266% | 258% | 150% |
| " | " | " | 20 nM | 257% | 254% | 159% |
| 23178 | 107 | control | 5 nM | 96% | 123% | 96.5% |
| " | " | " | 10 nM | 70.2% | 116% | 87.1% |
| " | " | " | 20 nM | 56% | 106% | 73.3% |

Example 8

Effect of STAT3 Antisense Oligonucleotides in a Murine Model for Rheumatoid Arthritis Collagen-induced arthritis (CIA) is used as a murine model for arthritis (Mussener, A., et al., *Clin. Exp. Immunol.*, 1997, 107, 485–493). Female DBA/1LacJ mice (Jackson Laboratories, Bar Harbor, Me.) between the ages of 6 and 8 weeks are used to assess the activity of STAT3 antisense oligonucleotides.

On day 0, the mice are immunized at the base of the tail with 100 μg of bovine type II collagen which is emulsified in Complete Freund's Adjuvant (CFA). On day 7, a second booster dose of collagen is administered by the same route. On day 14, the mice are injected subcutaneously with 100 μg of LPS. Oligonucleotide is administered intraperitoneally daily (10 mg/kg bolus) starting on day −3 and continuing for the duration of the study.

Weights are recorded weekly. Mice are inspected daily for the onset of CIA. Paw widths are rear ankle widths of affected and unaffected joints and are measured three times a week using a constant tension caliper. Limbs are clinically evaluated and graded on a scale from 0–4 (with 4 being the highest).

Example 9

Effect of STAT3 Antisense Oligonucleotides on Growth of Human MDA-MB231 Tumors in Nude Mice MDA-MB231 human breast carcinoma cells are obtained from the American Type Culture Collection (Bethesda, Md.). Serially transplanted MDA-MB231 tumors are established subcutaneously in nude mice. Beginning two weeks later, STAT3 antisense oligonucleotides, in saline, are administered intravenously daily for 14 days at dosages of 60 mg/kg and 6 mg/kg. Control oligonucleotides are also administered at these doses, and a saline control is also given. Tumor growth rates are monitored for the two-week period of oligonucleotide administration. Activity of the STAT3 antisense oligonucleotides is measured by a reduction in tumor growth. A lower-dose study can also be conducted using the same oligonucleotides at 6 mg/kg and 0.6 mg/kg.

Example 10

Effect of STAT3 Antisense Oligonucleotides on U-87 Human Glioblastoma Cells Following Subcutaneous Xenografts into Nude Mice The U-87 human glioblastoma cell line is obtained from the ATCC (Rockville Md.) and maintained in Iscove's DMEM medium supplemented with heat-inactivated 10% fetal calf serum. Nude mice are injected subcutaneously with $2 \times 10^7$ cells. Mice are injected intraperitoneally with STAT3 antisense oligonucleotides at dosages of either 2 mg/kg or 20 mg/kg for 21 consecutive days beginning 7 days after xenografts are implanted. Tumor volumes are measured on days 14, 21, 24, 31 and 35. Activity is measured by reduced tumor volume compared to saline or sense oligonucleotide control.

Example 11

Effect of STAT3 Antisense Oligonucleotides on Intracerebral U-87 Glioblastoma Xenografts into Nude Mice U-87 cells are implanted in the brains of nude mice. Mice are treated via continuous intraperitoneal administration of STAT3 antisense oligonucleotides at 20 mg/kg, control sense oligonucleotide (20 mg/kg) or saline beginning on day 7 after xenograft implantation. Activity of the STAT3 antisense oligonucleotides is measured by an increase in survival time compared to controls.

Example 12

Additional Antisense Oligonucleotides Targeted to Human STAT3

An additional set of oligonucleotides targeted to SEQ ID NO: 1 was designed and synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides (shown in bold). The internucleoside (backbone) linkages are phosphorothioate (P=S) throughout the oligonucleotide. All 2'-MOE cytosines and 2'-deoxy cytosines were 5-methyl-cytosines. These oligonucleotide sequences are shown in Table 9.

TABLE 9

Nucleotide Sequences of Additional Chimeric (deoxy gapped) Phosphorothioate Oligonucleotides targeted to Human STAT3

| ISIS NO. | NUCLEOTIDE SEQUENCE (5'→3') | TARGET GENE NUCLEOTIDE CO-ORDINATES[2] | GENE TARGET REGION | SEQ ID NO: |
|---|---|---|---|---|
| 113169 | ATGTGATTCTTTGCTGGCCG | 357 | 5' UTR | 108 |
| 113170 | AGCTGATTCCATTGGGCCAT | 221 | AUG | 109 |
| 113171 | CCAGGAGATTATGAAACACC | 385 | Coding | 110 |

TABLE 9-continued

Nucleotide Sequences of Additional Chimeric
(deoxy gapped) Phosphorothioate
Oligonucleotides targeted to Human STAT3

| ISIS NO. | NUCLEOTIDE SEQUENCE (5' ->3') | TARGET GENE NUCLEOTIDE CO-ORDINATES[2] | GENE TARGET REGION | SEQ ID NO: |
|---|---|---|---|---|
| 113172 | ACCGTGTGTCAAGCTGCTGT | 241 | Coding | 111 |
| 113173 | CCATTGGGAAGCTGTCACTG | 286 | Coding | 112 |
| 113174 | TGTGATTCTTTGCTGGCCGC | 356 | Coding | 113 |
| 113175 | GCGGCTATACTGCTGGTCAA | 411 | Coding | 114 |
| 113176 | GCTCCAGCATCTGCTGCTTC | 637 | Coding | 115 |
| 113177 | GATTCTTCCCACAGGCACCG | 539 | Coding | 116 |
| 113178 | TGATTCTTCCCACAGGCACC | 540 | Coding | 117 |
| 113179 | ATCCTGAAGGTGCTGCTCCA | 651 | Coding | 118 |
| 113180 | CGGACATCCTGAAGGTGCTG | 656 | Coding | 119 |
| 113181 | CCCGCCAGCTCACTCACGAT | 869 | Coding | 120 |
| 113182 | AGTCAGCCAGCTCCTCGTCC | 928 | Coding | 121 |
| 113183 | CCAGTCAGCCAGCTCCTCGT | 930 | Coding | 122 |
| 113184 | CGCCTCTTCCAGTCAGCCAG | 938 | Coding | 123 |
| 113185 | GGCCGGTGCTGTACAATGGG | 1109 | Coding | 124 |
| 113186 | ATCCTCTCCTCCAGCATCGG | 1127 | Coding | 125 |
| 113187 | CCGCTCCACCACAAAGGCAC | 1176 | Coding | 126 |
| 113188 | CGTCCCCAGAGTCTTTGTCA | 1324 | Coding | 127 |
| 113189 | TTGTGTTTGTGCCCAGAATG | 1375 | Coding | 128 |
| 113190 | GCTCGGCCCCCATTCCCACA | 1472 | Coding | 129 |
| 113191 | AGGCATTTGGCATCTGACAG | 1621 | Coding | 130 |
| 113192 | CTTGGGATTGTTGGTCAGCA | 1665 | Coding | 131 |
| 113193 | CTCGGCCACTTGGTCCCAGG | 1719 | Coding | 132 |
| 113194 | CCCCGCTTGGTGGTGGACGA | 1757 | Coding | 133 |
| 113195 | CCCCCGCTTGGTGGTGGACG | 1758 | Coding | 134 |
| 113196 | GGAGAAGCCCTTGCCAGCCA | 1881 | Coding | 135 |
| 113197 | TTCATTCCAAAGGGCCAAGA | 1947 | Coding | 136 |
| 113198 | CCCGCTCCTTGCTGATGAAA | 1981 | Coding | 137 |
| 113199 | GTGCTCAAGATGGCCCGCTC | 2000 | Coding | 138 |
| 113200 | CCCAAGTGAAAGTGACGCCT | 2071 | Coding | 139 |
| 113201 | ACCCAAGTGAAAGTGACGCC | 2072 | Coding | 140 |
| 113202 | CCGAATGCCTCCTCCTTGGG | 2252 | Coding | 141 |
| 113203 | GCCGACAATACTTCCCGAAT | 2266 | Coding | 142 |
| 113204 | GATGCTCCTGGCTCTCTGCC | 2284 | Coding | 143 |
| 113205 | TCAATGAATCTAAAGCGCGG | 2404 | Coding | 144 |
| 113206 | GACTCAAACTGCCCTCCTGC atcacccaca ttcactcatt | 2462 | Coding | 145 |
| 113207 | ATCACCCACATTCACTCATT | 2710 | 3' UTR | 146 |
| 113208 | AAAAGTGCCCAGATTGC | 2682 | 3' UTR | 147 |
| 113209 | AAAAGTGCCCAGATTGCTCA | 2679 | 3' UTR | 148 |
| 113210 | TAAAAGTGCCCAGATTGCTC | 2680 | 3' UTR | 149 |
| 113211 | AAGCAGATCACCCACATTCA | 2716 | 3' UTR | 150 |

These oligonucleotides were screened by Northern blot analysis in U266 cells at an oligonucleotide concentration of 2.5 μM. U266 human myeloma cell lines (originally obtained from American Type Culture Collection) were maintained in RPMI 1640 medium supplemented with 10% fetal calf serum. Cells (15×10⁶ cells in PBS) were transfected with oligonucleotides at 200 V with a single 6-millisecond pulse using a BTX Electro Square Porator T820 (Genetronics, San Diego Calif.). The cells were incubated for 24 hours before RNA extraction.

Total cellular RNA was isolated using the Rneasy kit (Qiagen, Santa Clarita, Calif.). Northern blottin was perfomed on 15 μg of RNA using a cDNA probe prepared from MB-MDA 468 RNA by standard RT-PCR followed by a nested primer reaction. Signals were quantitated using a Molecular Dynamics Phosphorimager.

Results for selected compounds (expressed as percent of control mRNA expression and percent inhibition of mRNA expression) are shown in Table 10.

TABLE 10

Inhibition of Human STAT3 mRNA expression in U266 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| None | — | — | 100 | — |
| 17148 | 95 | Coding | 95.1 | 4.9 |
| 17152 | 99 | 3' UTR | 82.5 | 17.5 |
| 113170 | 109 | AUG | 89.6 | 10.4 |
| 113171 | 110 | Coding | 110.2 | — |
| 113172 | 111 | Coding | 96.1 | 3.9 |
| 113173 | 112 | Coding | 119 | — |
| 113175 | 114 | Coding | 75.8 | 24.2 |
| 113176 | 115 | Coding | 72.3 | 27.7 |
| 113178 | 117 | Coding | 143.9 | — |
| 113181 | 120 | Coding | 105.4 | — |
| 113184 | 123 | Coding | 104.3 | — |
| 113187 | 126 | Coding | 55.9 | 44.1 |
| 113189 | 128 | Coding | 163.9 | — |
| 113199 | 139 | Coding | 64.4 | 35.6 |
| 113207 | 146 | 3' UTR | 123.6 | — |
| 113209 | 148 | 3' UTR | 71.4 | 28.6 |
| 113210 | 149 | 3' UTR | 72.2 | 27.8 |
| 113211 | 150 | 3' UTR | 116.5 | — |

Dose-response experiments were conducted for ISIS 113176, 129987, 113187, 129991, 113209, 129995, 113210 and 129999 as well as ISIS 17148 and the mouse STAT3 oligo ISIS 114054. Results are shown in Table 11.

TABLE 11

Percent inhibition of human STAT3 mRNA expression with antisense oligonucleotides - dose response

| ISIS # | SEQ ID NO: | Percent inhibition of STAT3 expression Oligo concentration | | |
|---|---|---|---|---|
| | | 2.5 μM | 5 μM | 10 μM |
| 17148 | 95 | 8 | 54 | 60 |
| 114054 | | 4 | 17 | 15 |
| 113176 | | 33 | 67 | 79 |
| 129987 | | 5 | 5 | 29 |
| 113187 | | 44 | 56 | 75 |
| 129991 | | 21 | 22 | 26 |
| 113209 | | 43 | 54 | 73 |
| 129995 | | 5 | 32 | 25 |
| 113210 | | 36 | 50 | 76 |
| 129999 | | 31 | 8 | — |

ISIS 17148, 113176, 113187, 113209 and 113210 were shown to reduce STAT3 expression by over 50% at one or more oligonucleotide concentrations. These compounds are therefore preferred.

Example 13

Antisense Inhibition of STAT3 Causes Apoptotic Cell Death in Mouse Melanoma Cells Mouse B16 melanoma cells were grown in RPMI 1640 (Life Technologies, Inc., Grand Island, N.Y.) medium supplemented with 10% fetal bovine serum, 2 mM L-glutamine, 1 mM sodium pyruvate, 1% MEM nonessential amino acids and 100 IU/ml penicillin/streptomycin.

Cells were treated with ISIS 17152, targeted to mouse STAT3, or the 3-base mismatch control, ISIS 28084 (AAAAAGAGGCCTGATTGCCC; SEQ ID NO: 151). Cells were transfected with oligonucleotide using LipofectAMINE PLUSJ reagent (GibcoBRL). Oligonucleotide was pre-complexed with LipofectAMINE PLUSJ by adding the oligonucleotide to 100 µl serum-free RPMI 1640 medium, then 6 µl LipofectAMINE PLUSJ reagent was added, the sample was mixed well and incubated for 15 minutes at room temperature. An additional 4 µl of LipofectAMINE PLUSJ reagent was diluted to 100 µl in serum-free RPMI. This diluted LipofectAMINE PLUSJ was mixed with the pre-complexed oligonucleotide/LipofectAMINE PLUSJ mixture and incubated for 15 minutes at room temperature. 800 µl of serum-free RPMI 1640 was added, and the resulting oligonucleotide-LipofectAMINE PLUSJ-medium mixture (approximately 1 ml) was added to cells in a 6-well plate. After 3 hours incubation, 1 ml of RPMI 1640 supplemened with 20% fetal bovine serum was added. Oligonucleotide concentrations were 200 nM or 300 nM.

24 hours after transfection, cells were counted to determine the effect of antisense treatment on cell death. Cells were harvested at 24 hours post transfection for western blot analysis and at 48 hours post-transfection for Annexin-V staining for apoptosis.

Effects of oligonucleotide on cell number are shown in Table 12.

TABLE 12

Effect of antisense inhibition of STAT3 on cell number

| | 200 nM | | 300 nM | |
|---|---|---|---|---|
| Expt | ISIS 28084 (3 mismatch) | ISIS 17152 | ISIS 28084 (3 mismatch) | ISIS 17152 |
| 1 | $10.2 \times 10^5$ | $3.8 \times 10^5$ | | |
| 2 | $5.0 \times 10^5$ | $6.8 \times 10^5$ | $9.1 \times 10^5$ | $3.5 \times 10^5$ |
| 3 | $3.5 \times 10^5$ | $1.8 \times 10^5$ | $3.3 \times 10^5$ | $2.2 \times 10^5$ |

Thus treatment with STAT3 antisense oligonucleotide increased cell death (decreased cell number).

Apoptosis in B16 cells was measured by staining with Annexin V-PE (Clontech) and flow cytometry analysis 48 hours after antisense treatment. Positive staining for Annexin-V indicates apoptosis is occurring. Mock-transfected cells and control oligonucleotide-treated cell cultures had 11.37% and 10.15% of cells staining positive for Annexin-V. In contrast, ISIS 17152-treated cells were 29.84% positive for Annexin-V, indicating a nearly threefold increase in apoptotic cells. It should be noted that in general, the percent of apoptosis in B16 cells is likely to have been underestimated since detached dead cells are washed off in processing.

Western blot analysis was done on cells 24 hours after antisense treatment, using an anti-STAT3 antibody (K15, Santa Cruz Biotechnology, Santa Cruz, Calif.). ISIS 17152 at 200 nM or 300 nM significantly reduced STAT3 protein production in B16 cells.

Example 14

Effect of STAT3 Antisense Oligonucleotides on Melanoma Tumors

Six-week-old female C57BL mice were purchased from the National Cancer Center (Frederick Md.) and maintained under approved conditions. Mice were shaved in the left flank area and injected subcutaneously with $2 \times 10^5$ B16 melanoma cells in 100 µl of PBS. After 7–10 days, B16 tumors with a diameter of 3–6 mm were established. Tumor volume was calculated according to the formula $V = 0.52 \times a^2 \times b$ (a, smallest superficial diameter; b, largest superficial diameter).

Beginning two weeks later, STAT3 antisense oligonucleotides, in saline, are administered intravenously daily for 14 days at dosages of 60 mg/kg and 6 mg/kg. Control oligonucleotides are also administered at these doses, and a saline control is also given. Tumor growth rates are monitored for the two-week period of oligonucleotide administration. Activity of the STAT3 antisense oligonucleotides is measured by a reduction in tumor growth. A lower-dose study can also be conducted using the same oligonucleotides at 6 mg/kg and 0.6 mg/kg.

Example 15

Effect of STAT3 Antisense Oligonucleotides on Leukemic Large Granular Lymphocytes (LGL)

LGL leukemia is a lymphoproliferative disease with autoimmune features and LGL cells are known to be insensitive to Fas-dependent cell death despite high levels of Fas and FasL expression. (Lamy et al., Blood, 1998, 92, 4771–7). STAT3 antisense oligonucleotides were tested for their ability to sensitize LGL cells to the apoptotic signal in these cells.

LGL leukemic cells were obtained from patients who met the clinical criteria of T cell (CD3+) LGL leukemia with increased LGL counts and clonal TCR gene rearrangements. All patients had chronic disease not requiring treatment at the time of analysis. Purified leukemic LGL cells were placed in 24-well plates at a concentration of $2 \times 10^6/0.5$ mL of complete medium (RPMI-1640 medium supplemented with 10% fetal bovine serum, 2 mM L-glutamine, 10 U/mL penicillin, and 100 ug/mL streptomycin, all from Gibco Life Technologies, Gaithersburg, Md.). Cells were incubated with either ISIS 17148 antisense oligonucleotide (SEQ ID NO: 95) or the control, ISIS 16094 (SEQ ID NO: 152). Antisense oligonucleotide delivery to LGL leukemic cells was by passive uptake and no transfection reagents were included in the reaction. Both ISIS 17148 and ISIS 16094 are 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All 2'-MOE cytosines and 2'-deoxy cytosines were 5-methyl-cytosines.

Extracts of LGL cells treated with antisense oligonucleotides (1 uM dosing for ISIS 17148 and the control) from three patients were obtained and assayed for STAT3 protein levels by Western blot. Sensitization of the LGL cells to Fas-mediated apoptosis was also measured by flow cytometry in cells treated with antisense oligonucleotides at doses of 1, 2 and 5 uM. By Western analysis, a reduction in STAT3 protein levels ranged from 25 to 45%. Sensitivity to Fas-mediated apoptosis was also significantly increased in the antisense treated cells and was dose dependent. Measurements of percent specific apoptosis in duplicate reactions revealed an increase in apoptosis from 5% in untreated cells to levels of 6, 17 and 24% in antisense-treated cells at 1, 2, and 5 uM, respectively. Levels of apoptosis in control oligonucleotide treated cells remained at 6% at all doses.

What is claimed is:

1. An antisense compound 20 to 30 nucleobases in length targeted to nucleobases 637–656 and 1669–1688 of human STAT3 (SEQ ID NO: 1), wherein said antisense compound inhibits the expression of human STAT3.

2. The antisense compound of claim 1 which is an antisense oligonucleotide.

3. The antisense compound of claim 2 wherein the antisense oligonucleotide comprises at least one modified internucleoside linkage.

4. The antisense compound of claim 3 wherein the modified internucleoside linkage is a phosphorothioate linkage.

5. The antisense compound of claim 2 wherein the antisense oligonucleotide comprises at least one modified sugar moiety.

6. The antisense compound of claim 5 wherein the modified sugar moiety is a 2'-O-methoxyethyl moiety.

7. The antisense compound of claim 2 wherein the antisense oligonucleotide comprises at least one modified nucleobase.

8. The antisense compound of claim 7 wherein modified nucleobase is a 5-methyl cytosine.

9. The antisense compound of claim 1 wherein the antisense oligonucleotide is a chimeric oligonucleotide.

10. A composition comprising the antisense compound of claim 1 and a pharmaceutically acceptable carrier or diluent.

11. The composition of claim 10 further comprising a colloidal dispersion system.

12. The composition of claim 10 wherein the antisense compound is an antisense oligonucleotide.

13. A method of inhibiting the expression of STAT3 in human cells or tissues comprising contacting said cells or tissue in vitro or ex vitro with the antisense compound of claim 1 so that expression of STAT3 is inhibited.

14. A method of inducing apoptosis in a cell comprising contacting a cell in vitro or ex vivo with the antisense compound of claim 1 so that apoptosis is induced.

15. The method of claim 14 wherein said apoptosis is Fas-mediated.

* * * * *

UNITED STATES PATENT AND TRADEMARK OFFICE
CERTIFICATE OF CORRECTION

PATENT NO. : 6,727,064 B2
DATED : April 27, 2004
INVENTOR(S) : James G. Karras

It is certified that error appears in the above-identified patent and that said Letters Patent is hereby corrected as shown below:

Column 87,
Line 33, please delete "An antisense compound 20 to 30 nucleobases in length targeted to nucleobases 637-656 and 1669-1688 of human STAT3 (SEQ ID NO: 1), wherein said antisense compound inhibits the expression of human STAT 3." and insert therefor -- An antisense compound 20 to 30 nucleobases in length targeted to nucleobases 637-656 of human STAT3 (SEQ ID NO: 1), wherein said antisense compound inhibits the expression of human STAT3. --;

Column 88,
Line 45, please delete "ex vitro" and insert therefor -- ex vivo --.

Signed and Sealed this

Sixth Day of July, 2004

JON W. DUDAS
*Acting Director of the United States Patent and Trademark Office*

SEQUENCE LISTING

<160> NUMBER OF SEQ ID NOS: 152

<210> SEQ ID NO 1
<211> LENGTH: 2787
<212> TYPE: DNA
<213> ORGANISM: Homo sapiens

<400> SEQUENCE: 1

| | | | | | |
|---|---|---|---|---|---|
| cagctggaat | tcggggcggc | ggcgcagact | gggaggggga | gccggggtt | ccgacgtcgc | 60 |
| agccgaggga | acaagcccca | accggatcct | ggacaggcac | cccggcttgg | cgctgtctct | 120 |
| cccctcggc | tcggagaggc | ccttcggcct | gagggagcct | cgccgcccgt | ccccggcaca | 180 |
| cgcgcagccc | cggcctctcg | gcctctgccg | gagaaacagg | atgcccaat | ggaatcagct | 240 |
| acagcagctt | gacacacggt | acctggagca | gctccatcag | ctctacagtg | acagcttccc | 300 |
| aatggagctg | cggcagtttc | tggccccttg | gattgagagt | caagattggg | catatgcggc | 360 |
| cagcaaagaa | tcacatgcca | ctttggtgtt | tcataatctc | ctgggagaga | ttgaccagca | 420 |
| gtatagccgc | ttcctgcaag | agtcgaatgt | tctctatcag | cacaatctac | gaagaatcaa | 480 |
| gcagtttctt | cagagcaggt | atcttgaaga | gccaatggag | attgcccgga | ttgtggcccg | 540 |
| gtgcctgtgg | gaagaatcac | gccttctaca | gactgcagcc | actgcggccc | agcaagggg | 600 |
| ccaggccaac | caccccacag | cagccgtggt | gacggagaag | cagcagatgc | tggagcagca | 660 |
| ccttcaggat | gtccggaaga | gagtgcagga | tctagaacga | aaaatgaaag | tggtagagaa | 720 |
| tctccaggat | gactttgatt | tcaactataa | aaccctcaag | agtcaaggag | acatgcaaga | 780 |
| tctgaatgga | aacaaccagt | cagtgaccag | gcagaagatg | cagcagctgg | aacagatgct | 840 |
| cactgcgctg | gaccagatgc | ggagaagcat | cgtgagtgag | ctggcgggc | ttttgtcagc | 900 |
| gatggagtac | gtgcagaaaa | ctctcacgga | cgaggagctg | gctgactgga | gaggcggca | 960 |
| acagattgcc | tgcattggag | gcccgcccaa | catctgccta | gatcggctag | aaaactggat | 1020 |
| aacgtcatta | gcagaatctc | aacttcagac | ccgtcaacaa | attaagaaac | tggaggagtt | 1080 |
| gcaccaaaaa | gtttcctaca | aggggaccc | cattgtacag | caccggccga | tgctggagga | 1140 |
| gaggatcgtg | gagctgttca | gaaacttaat | gaaaagtgcc | tttgtggtgg | agcggcagcc | 1200 |
| ctgcatgccc | atgcatcctg | accggcccct | cgtcatcaag | accggcgtcc | agttcactac | 1260 |
| taaagtcagg | ttgctggtca | agttccctga | gttgaattat | cagcttaaaa | ttaaagtgtg | 1320 |
| cattgacaaa | gactctgggg | acgttgcagc | tctcagagga | tcccggaaat | taacattct | 1380 |
| gggcacaaac | acaaagtga | tgaacatgga | agaatccaac | aacggcagcc | tctctgcaga | 1440 |
| attcaaacac | ttgaccctga | gggagcagag | atgtgggaat | gggggccgag | ccaattgtga | 1500 |
| tgcttccctg | attgtgactg | aggagctgca | cctgatcacc | tttgagaccg | aggtgtatca | 1560 |
| ccaaggtctc | aagattgacc | tagagaccca | ctccttgtca | gttgtggtga | tctccaacat | 1620 |
| ctgtcagatg | ccaaatgcct | gggcgtccat | cctgtggtac | aacatgctga | ccaacaatcc | 1680 |
| caagaatgtg | aacttcttca | ctaagccgcc | aattggaacc | tgggaccaag | tggccgaggt | 1740 |
| gctcagctgg | cagttctcgt | ccaccaccaa | gcggggctg | agcatcgagc | agctgacaac | 1800 |
| gctggctgag | aagctcctag | gcctggtgt | gaactactca | gggtgtcaga | tcacatgggc | 1860 |
| taacttctgc | aaagaaaaca | tggctggcaa | gggcttctcc | tactgggtct | ggctagacaa | 1920 |
| tatcatcgac | cttgtgaaaa | agtatatctt | ggcccttttgg | aatgaagggt | acatcatggg | 1980 |
| tttcatcagc | aaggagcggg | agcgggccat | cttgagcact | aagccccag | gcaccttcct | 2040 |

```
gctgcgcttc agtgaaagca gcaaagaagg aggcgtcact ttcacttggg tggagaagga    2100
catcagcggt aagacccaga tccagtccgt ggaaccatac acaaagcagc agctgaacaa    2160
catgtcattt gctgaaatca tcatgggcta taagatcatg gatgctacca atatcctgtt    2220
gtctccactt gtctatctct atcctgacat tcccaaggag gaggcattcg ggaagtattg    2280
tcggccagag agccaggagc atcctgaagc tgacccaggt agcgctgccc cataccctgaa   2340 gaccaagttt atctgtgtga caccaacgac ctgcagcaat accattgacc tgccgatgtc    2400
cccccgcgct ttagattcat tgatgcagtt tggaaataat ggtgaaggtg ctgaaccctc    2460
agcaggaggg cagtttgagt ccctcacctt tgacatggag ttgacctcgg agtgcgctac    2520
ctcccccatg tgaggagctg agaacggaag ctgcagaaaa tacgactga ggcgcctacc     2580 tgcattctgc caccctcac acagccaaac cccagatcat ctgaaactac taactttgtg     2640
gttccagatt ttttttaatc tcctacttct gctatctttg agcaatctgg gcactttta     2700 aaatagagaa atgagtgaat gtgggtgatc tgcttttatc taaatgcaaa taaggatgtg    2760
ttctctgaga cccatgatca ggggatg                                       2787

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 2
gtctgcgccg ccgccccgaa                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 3
ggccgaaggg cctctccgag                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 4
tcctgtttct ccggcagagg                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 5
catcctgttt ctccggcaga                                                 20

<210> SEQ ID NO 6
<211> LENGTH: 20
<212> TYPE: DNA
```

<213> ORGANISM: Artificial Sequence
<220> FEATURE:
<223> OTHER INFORMATION: Description of Artificial Sequence: Synthetic

<400> SEQUENCE: 6
gccatcctgt ttctccggca                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 7
gggccatcct gtttctccgg                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 8
ttgggccatc ctgtttctcc                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 9
cattgggcca tcctgtttct                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 10
tccattgggc catcctgttt                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 11
attccattgg gccatcctgt                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 12
tgattccatt gggccatcct                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
gctgattcca ttgggccatc                                          20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 14
tagctgattc cattgggcca                                          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 15
tgtagctgat tccattgggc                                          20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 16
ctgtagagct gatggagctg                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 17
cccaatcttg actctcaatc                                          20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 18
cccaggagat tatgaaacac                                          20

<210> SEQ ID NO 19
<211> LENGTH: 20
<212> TYPE: DNA
<213> ORGANISM: Artificial Sequence
<220> FEATURE:

```
<223> OTHER INFORMATION: Description of Artificial Sequence: Synthetic

<400> SEQUENCE: 19
acattcgact cttgcaggaa                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 20
tctgaagaaa ctgcttgatt                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 21
ggccacaatc cgggcaatct                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 22
tggctgcagt ctgtagaagg                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 23
ctgctccagc atctgctgct                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 24
tttctgttct agatcctgca                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 25
tagttgaaat caaagtcatc                                                    20
```

```
<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 26
ttccattcag atcttgcatg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 27
tctgttccag ctgctgcatc                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 28
tcactcacga tgcttctccg                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 29
gagttttctg cacgtactcc                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 30
atctgttgcc gcctcttcca                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 31
ctagccgatc taggcagatg                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
```

<400> SEQUENCE: 32
cgggtctgaa gttgagattc                                           20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 33
cggccggtgc tgtacaatgg                                           20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 34
tttcattaag tttctgaaca                                           20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 35
aggatgcatg ggcatgcagg                                           20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 36
gaccagcaac ctgactttag                                           20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 37
atgcacactt taattttaag                                           20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 38
ttccgggatc ctctgagagc                                           20

<210> SEQ ID NO 39
<211> LENGTH: 20

```
<212> TYPE: DNA
<213> ORGANISM: Artificial Sequence
<220> FEATURE:
<223> OTHER INFORMATION: Description of Artificial Sequence: Synthetic

<400> SEQUENCE: 39
ttccatgttc atcacttttg                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 40
gtcaagtgtt tgaattctgc                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 41
caatcaggga agcatcacaa                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 42
tacacctcgg tctcaaaggt                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 43
tgacaaggag tgggtctcta                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 44
cgcccaggca tttggcatct                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 45
```
cattcttggg attgttggtc                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 46
cacttggtcc caggttccaa                                                    20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 47
cccgcttggt ggtggacgag                                                    20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 48
agttcacacc aggccctagg                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 49
gttttctttg cagaagttag                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 50
atattgtcta gccagaccca                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 51
aacccatgat gtacccttca                                                    20

<210> SEQ ID NO 52
<211> LENGTH: 20
<212> TYPE: DNA
<213> ORGANISM: Artificial Sequence

```
<220> FEATURE:
<223> OTHER INFORMATION: Description of Artificial Sequence: Synthetic

<400> SEQUENCE: 52
gcttagtgct caagatggcc                                          20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 53
gctgctttca ctgaagcgca                                          20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 54
gtgaaagtga cgcctccttc                                          20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 55
ctgatgtcct tctccaccca                                          20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 56
actggatctg ggtcttaccg                                          20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 57
aaatgacatg ttgttcagct                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 58
gcccatgatg atttcagcaa                                          20
```

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 59
tattggtagc atccatgatc                                                   20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 60
atagacaagt ggagacaaca                                                   20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 61
ttgggaatgt caggatagag                                                   20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 62
ctcctggctc tctggccgac                                                   20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 63
acctgggtca gcttcaggat                                                   20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 64
cacagataaa cttggtcttc                                                   20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 65
atcggcaggt caatggtatt                                               20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 66
ccaaactgca tcaatgaatc                                               20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 67
ggttcagcac cttcaccatt                                               20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 68
gagggactca aactgccctc                                               20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 69
caactccatg tcaaaggtga                                               20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 70
ttctcagctc ctcacatggg                                               20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 71
cgttctcagc tcctcacatg                                               20

<210> SEQ ID NO 72

```
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 72
tccgttctca gctcctcaca                                           20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 73
cttccgttct cagctcctca                                           20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 74
agcttccgtt ctcagctcct                                           20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 75
agaatgcagg taggcgcctc                                           20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 76
accacaaagt tagtagtttc                                           20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 77
tgctcaaaga tagcagaagt                                           20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 78
```
attcactcat ttctctattt                                                20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 79
catttagata aaagcagatc                                                20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 80
acatccttat ttgcatttag                                                20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 81
gatcatgggt ctcagagaac                                                20

<210> SEQ ID NO 82
<211> LENGTH: 2869
<212> TYPE: DNA
<213> ORGANISM: Mus musculus

<400> SEQUENCE: 82
gccgcgacca gccaggccgg ccagtcgggc tcagcccgga gacagtcgag acccctgact        60
gcagcaggat ggctcagtgg aaccagctgc agcagctgga cacacgctac ctgaagcagc       120
tgcaccagct gtacagcgac acgttcccca tggagctgcg gcagttcctg gcaccttgga       180
ttgagagtca agactgggca tatgcagcca gcaaagagtc acatgccacg ttggtgtttc       240
ataatctctt gggtgaaatt gaccagcaat atagccgatt cctgcaagag tccaatgtcc       300
tctatcagca caaccttcga gaatcaagc agtttctgca gagcaggtat cttgagaagc       360
caatggaaat tgcccggatc gtggcccgat gcctgtggga gagtctcgc ctcctccaga       420 cggcagccac ggcagcccag caaggggcc aggccaacca cccaacagcc gccgtagtga       480
cagagaagca gcagatgttg gagcagcatc ttcaggatgt ccggaagcga gtgcaggatc       540
tagaacagaa aatgaaggtg gtggagaacc tccaggacga ctttgatttc aactacaaaa       600
ccctcaagag ccaaggagac atgcaggatc tgaatgaaaa caaccagtct gtgaccagac       660
agaagatgca gcagctggaa cagatgctca cagccctgga ccagatgcgg agaagcattg       720
tgagtgagct ggcggggctc ttgtcagcaa tggagtacgt gcagaagaca ctgactgatg       780
aagagctggc tgactggaag aggcggcagc agatcgcgtg catcggaggc cctcccaaca       840
tctgcctgga ccgtctggaa aactggataa cttcattagc agaatctcaa cttcagaccc       900
gccaacaaat taagaaactg gaggagctgc agcagaaagt gtcctacaag ggcgaccta       960

-continued

```
tcgtgcagca ccggcccatg ctggaggaga ggatcgtgga gctgttcaga aacttaatga      1020
agagtgcctt cgtggtggag cggcagccct gcatgcccat gcacccggac cggcccttag      1080
tcatcaagac tggtgtccag tttaccacga aagtcaggtt gctggtcaaa tttcctgagt      1140
tgaattatca gcttaaaatt aaagtgtgca ttgataaaga ctctggggat gttgctgccc      1200
tcagagggtc tcggaaattt aacattctgg cacgaacac aaaagtgatg aacatggagg       1260
agtctaacaa cggcagcctg tctgcagagt tcaagcacct gacccttagg gagcagagat      1320
gtgggaatgg aggccgtgcc aattgtgatg cctccttgat cgtgactgag gagctgcacc      1380
tgatcacctt cgagactgag gtgtaccacc aaggcctcaa gattgaccta gagacccact      1440
ccttgccagt tgtggtgatc tccaacatct gtcagatgcc aaatgcttgg gcatcaatcc      1500
tgtggtataa catgctgacc aataacccca agaacgtgaa cttcttcact aagccgccaa      1560
ttggaacctg ggaccaagtg gccgaggtgc tcagctggca gttctcgtcc accaccaagc      1620
gagggctgag catcgagcag ctgacaacgc tggctgagaa gctcctaggg cctggtgtga      1680
actactcagg gtgtcagatc acatgggcta aattctgcaa agaaaacatg gctggcaagg      1740
gcttctcctt ctgggtctgg ctagacaata tcatcgacct tgtgaaaaag tatatcttgg      1800 cccttttggaa tgaagggtac atcatgggtt tcatcagcaa ggagcgggag cgggccatcc     1860
taagcacaaa gcccccgggc accttcctac tgcgcttcag cgagagcagc aaagaaggag      1920
gggtcacttt cacttgggtg aaaaggaca tcagtggcaa gacccagatc cagtctgtag       1980
agccatacac caagcagcag ctgaacaaca tgtcatttgc tgaaatcatc atgggctata     2040
agatcatgga tgcgaccaac atcctggtgt ctccacttgt ctacctctac cccgacattc      2100
ccaaggagga ggcatttgga aagtactgta ggcccgagag ccaggagcac cccgaagccg      2160
acccaggtag tgctgccccg tacctgaaga ccaagttcat ctgtgtgaca ccaacgacct      2220
gcagcaatac cattgacctg ccgatgtccc cccgcacttt agattcattg atgcagtttg      2280
gaaataacgg tgaaggtgct gagccctcag caggagggca gtttgagtcg ctcacgtttg      2340
acatggatct gacctcggag tgtgctacct cccccatgtg aggagctgaa accagaagct      2400
gcagagacgt gacttgagac acctgccccg tgctccaccc ctaagcagcc gaaccccata      2460
tcgtctgaaa ctcctaactt tgtggttcca gattttttt tttaatttcc tacttctgct       2520
atctttgggc aatctgggca ctttttaaaa gagagaaatg agtgagtgtg ggtgataaac      2580
tgttatgtaa agaggagaga cctctgagtc tggggatggg gctgagagca gaagggaggc      2640
aaaggggaac acctcctgtc ctgcccgcct gccctccttt ttcagcagct cggggggttgg     2700 ttgttagaca agtgcctcct ggtgcccatg gctacctgtt gccccactct gtgagctgat      2760
accccattct gggaactcct ggctctgcac tttcaacctt gctaatatcc acatagaagc      2820
taggactaag cccaggaggt tcctctttaa attaaaaaaa aaaaaaaaa                  2869
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 83
gttccactga gccatcctgc         20

<210> SEQ ID NO 84
<211> LENGTH: 20

```
<212> TYPE: DNA
<213> ORGANISM: Artificial Sequence
<220> FEATURE:
<223> OTHER INFORMATION: Description of Artificial Sequence: Synthetic

<400> SEQUENCE: 84
ttcaggtagc gtgtgtccag                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 85
atgtgactct ttgctggctg                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 86
ccaagagatt atgaaacacc                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 87
gctccaacat ctgctgcttc                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 88
gctcttcatc agtcagtgtc                                              20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 89
atctgacacc ctgagtagtt                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 90
```
gccagaccca gaaggagaag                                                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 91
cgctccttgc tgatgaaacc                                                    20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 92
aacttggtct tcaggtacgg                                                    20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 93
atcaatgaat ctaaagtgcg                                                    20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 94
tcagcacctt caccgttatt                                                    20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 95
actcaaactg ccctcctgct                                                    20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 96
ggtttcagct cctcacatgg                                                    20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 97
taaaaaaaaa aatctggaac                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 98
aagatagcag aagtaggaaa                                               20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 99
aaaaagtgcc cagattgccc                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 100
atcacccaca ctcactcatt                                               20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 101
cctttgcctc ccttctgctc                                               20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 102
tgaaaaagga gggcaggcgg                                               20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 103
caccaggagg cacttgtcta                                               20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 104
aacctcctgg gcttagtcct                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 105
aaaaagtgcg cagattgccc                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 106
aaaaagtccg ctgattgccc                                               20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 107
aaaaactccg ctgaatgccc                                               20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 108
atgtgattct ttgctggccg                                               20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 109
agctgattcc attgggccat                                               20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 110
ccaggagatt atgaaacacc                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 111
accgtgtgtc aagctgctgt                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 112
ccattgggaa gctgtcactg                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 113
tgtgattctt tgctggccgc                                              20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 114
gcggctatac tgctggtcaa                                              20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 115
gctccagcat ctgctgcttc                                              20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 116
gattcttccc acaggcaccg                                              20

<210> SEQ ID NO 117

```
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 117
tgattcttcc cacaggcacc                                                     20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 118
atcctgaagg tgctgctcca                                                     20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 119
cggacatcct gaaggtgctg                                                     20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 120
cccgccagct cactcacgat                                                     20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 121
agtcagccag ctcctcgtcc                                                     20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 122
ccagtcagcc agctcctcgt                                                     20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 123
```
cgcctcttcc agtcagccag                                                20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 124
ggccggtgct gtacaatggg                                                20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 125
atcctctcct ccagcatcgg                                                20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 126
ccgctccacc acaaaggcac                                                20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 127
cgtccccaga gtctttgtca                                                20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 128
ttgtgtttgt gcccagaatg                                                20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 129
gctcggcccc cattcccaca                                                20

<210> SEQ ID NO 130
<211> LENGTH: 20
<212> TYPE: DNA

<213> ORGANISM: Artificial Sequence
<220> FEATURE:
<223> OTHER INFORMATION: Description of Artificial Sequence: Synthetic

<400> SEQUENCE: 130
aggcatttgg catctgacag                                          20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 131
cttgggattg ttggtcagca                                          20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 132
ctcggccact tggtcccagg                                          20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 133
ccccgcttgg tggtggacga                                          20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 134
cccccgcttg gtggtggacg                                          20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 135
ggagaagccc ttgccagcca                                          20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 136
ttcattccaa agggccaaga                                          20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 137
cccgctcctt gctgatgaaa                                              20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 138
gtgctcaaga tggcccgctc                                              20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 139
cccaagtgaa agtgacgcct                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 140
acccaagtga aagtgacgcc                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 141
ccgaatgcct cctccttggg                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 142
gccgacaata cttcccgaat                                              20

<210> SEQ ID NO 143
<211> LENGTH: 20
<212> TYPE: DNA
<213> ORGANISM: Artificial Sequence
<220> FEATURE:

<223> OTHER INFORMATION: Description of Artificial Sequence: Synthetic

<400> SEQUENCE: 143
gatgctcctg gctctctggc                                            20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 144
tcaatgaatc taaagcgcgg                                            20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 145
gactcaaact gccctcctgc                                            20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 146
atcacccaca ttcactcatt                                            20

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 147
aaaagtgccc agattgc                                               17

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 148
aaaagtgccc agattgctca                                            20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 149
taaaagtgcc cagattgctc                                            20

-continued

```
<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 150
aagcagatca cccacattca                                               20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 151
aaaaagaggc ctgattgccc                                               20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 152
tctggcaaag tgtcagtatg                                               20
```